US00PP32292P2

(12) United States Plant Patent
Holtmaat

(10) Patent No.: US PP32,292 P2
(45) Date of Patent: Oct. 6, 2020

(54) ***ECHINACEA* PLANT NAMED 'YELLOW RAINBOW'**

(50) Latin Name: ***Echinacea* hybrid**
Varietal Denomination: Yellow Rainbow

(71) Applicant: AB-Kwekersrechten BV, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 16/501,671

(22) Filed: May 20, 2019

(30) Foreign Application Priority Data

Mar. 13, 2019 (QZ) ..... PBR 2019/0684

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./263.1, 428
See application file for complete search history.

(56) References Cited

PUBLICATIONS

AB Cultivars website (https://www.ab-cultivars.com/?portfolio=echinacea-yellow-rainbow-marcella). Retrieved Feb. 10, 2020. 6 pages. (Year: 2018).*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Echinacea* plant named 'Yellow Rainbow' that is characterized by its inflorescences with ray florets that are light yellow in color and fading into light pink at the base, its strong flowering stems, and its short plant height.

2 Drawing Sheets

Botanical classification: *Echinacea* hybrid.
Variety denomination: 'Yellow Rainbow'.

CROSS REFERENCE TO A RELATED APPLICATION

This application is related to U.S. Plant Patent for a plant derived from the same breeding program that is entitled *Echinacea* Plant Named 'Rainb299' (U.S. Plant Pat. No. 28,573).

BACKGROUND OF THE INVENTION

The present invention relates to a new and distinct cultivar of *Echinacea* of hybrid origin and will be referred to hereafter by its cultivar name 'Yellow Rainbow'. 'Yellow Rainbow' is an herbaceous perennial grown for landscape and container use.

The Inventor discovered the new cultivar as a naturally occurring branch mutation of *Echinacea* 'Rainb299' in June of 2017 that was growing in a trial field in Zuidwolde, The Netherlands.

Asexual propagation of the new cultivar was first accomplished under the direction of the Inventor by tissue culture using meristem tissue in March 2018 in Heerhugowaard, The Netherlands. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Yellow Rainbow' as unique cultivar of *Echinacea*.

1. 'Yellow Rainbow' exhibits inflorescences with ray florets that are light yellow in color and fading into light pink at the base.
2. 'Yellow Rainbow' exhibits strong flowering stems.
3. 'Yellow Rainbow' exhibits a short plant height.

The parent plant of 'Yellow Rainbow', 'Rainb299', differs from 'Yellow Rainbow' in having inflorescences with ray florets that are orange in color with a clear pink base. 'Yellow Rainbow' can also compared to the *Echinacea* cultivars 'Eglow' (U.S. Plant Pat. No. 24,801) and 'Cleopatra' (U.S. Plant Pat. No. 24,631). 'Eglow' is similar to 'Yellow Rainbow' in having inflorescences with bi-colored ray florets. 'Eglow' differs from 'Yellow Rainbow' in having inflorescences with ray florets that are orange-yellow in color with a red base and in having a much taller plant height. 'Cleopatra' is similar to 'Yellow Rainbow' in having a similar plant height and inflorescence size. 'Cleopatra' differs from 'Yellow Rainbow' in being less floriferous and in having inflorescences with ray florets that are yellow in color and not bi-colored.

BRIEF DESCRIPTION OF THE DRAWINGS

The accompanying colored photographs illustrate the overall appearance and distinct characteristics of the new *Echinacea*. The photographs were taken of a ten-month-old plant of the new cultivar as grown outdoors in 17-cm containers in Zuidwolde, The Netherlands.

The photograph in FIG. 1 illustrates the overall habit and appearance of 'Yellow Rainbow' in bloom.

Figure 1:
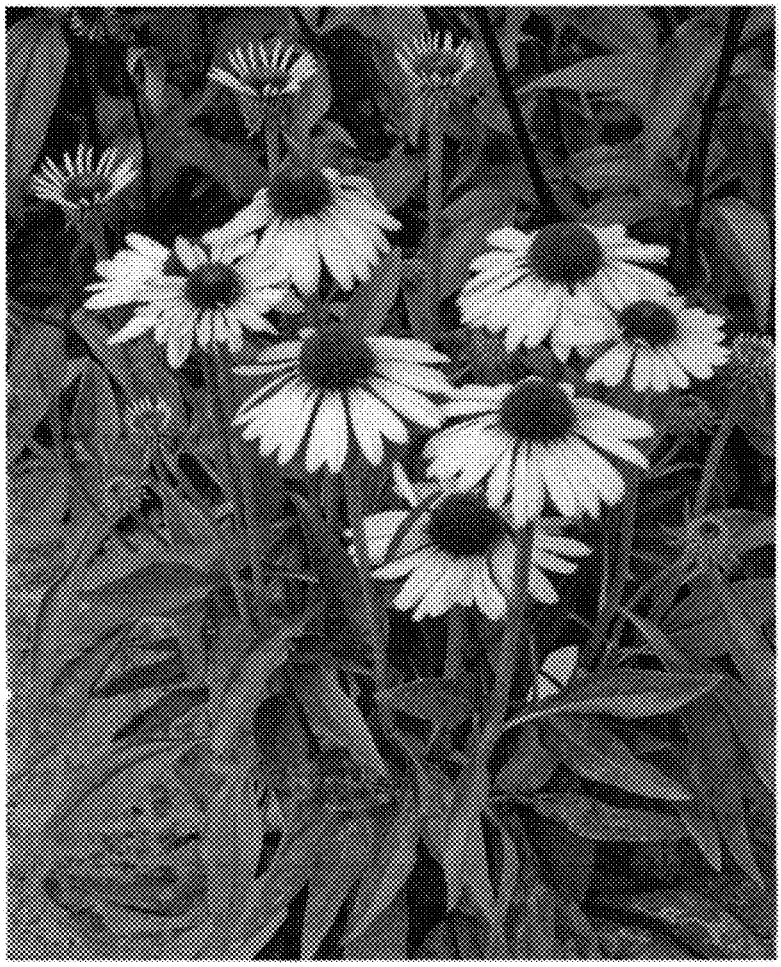
Figure 2:
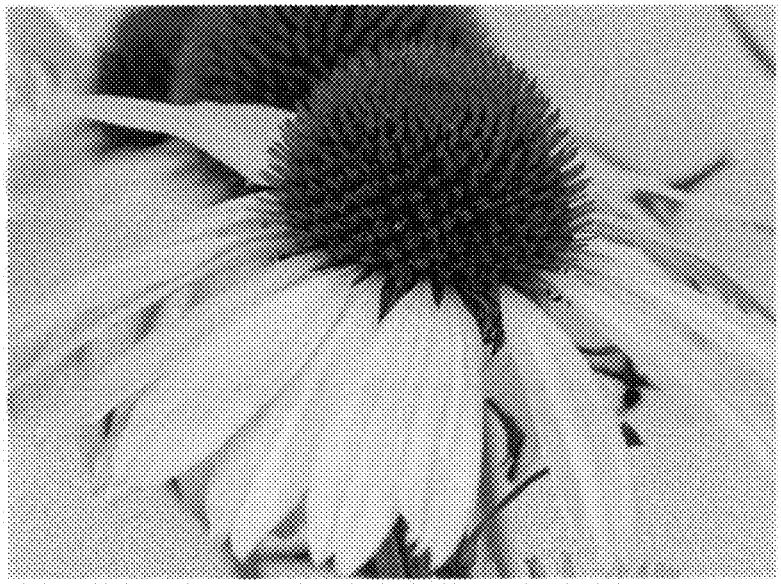

The photograph in FIG. 2 provides a close-up view of an inflorescence of 'Yellow Rainbow'.

Figure 3:
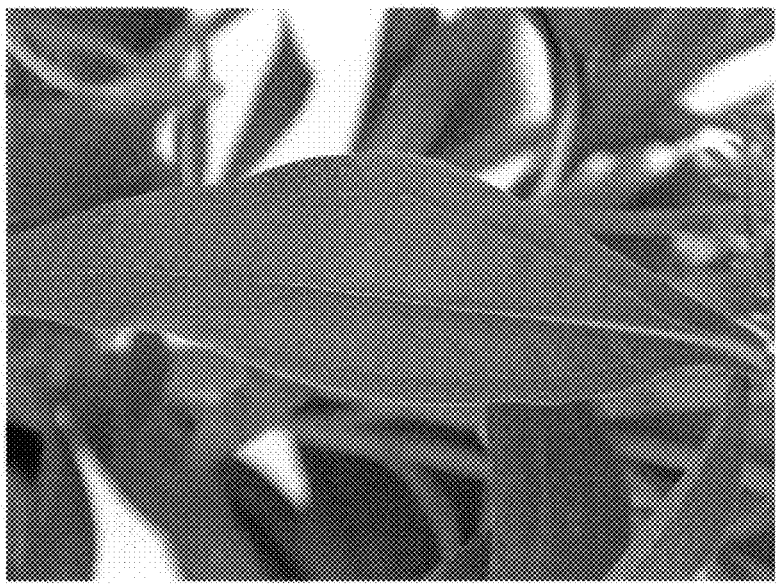

The photograph in FIG. 3 provides a close-up view of a leaf of 'Yellow Rainbow'.

The colors in the photographs are as close as possible with the photographic and printing technology utilized and color values cited in the detailed botanical description accurately describe the colors of the new *Echinacea*.

DETAILED BOTANICAL DESCRIPTION

The following is a detailed description of ten-month-old plants of the new cultivar as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms for 10 weeks from July to late September, in The Netherlands.

*Plant type*.—Herbaceous perennial.

*Plant habit*.—Compact, broad ovate in shape, upright.

*Height and spread*.—An average of 50 cm in height and spread.

*Hardiness*.—At least to U.S.D.A Zones 3.

*Disease and pest resistance*.—No susceptibility and resistance to diseases and pests has been observed.

*Root description*.—Fibrous and fine, 158D in color.

*Propagation*.—Tissue culture using meristem tissue.

*Growth rate*.—Moderate.

*Root development*.—Rooting occurs in about 10 weeks and a young rooted plant can be produced in about 3 months.

Stem description:

*Shape*.—Rounded.

*Stem color*.—144B and moderately marbled 143C.

*Stem size*.—Average of flowering stem (to base of uppermost leaf) 25 cm in length, 6.5 mm in diameter.

*Stem strength*.—Very strong.

*Stem aspect*.—Grow at an average angle of 20° from the base (0°=vertical).

*Stem surface*.—Moderately to densely covered with very short strigose hairs; an average of 0.3 mm in length and 157D in color.

*Stem number*.—Average of 5 main basal branches.

*Internode length*.—Average of 4.3 cm.

*Branching*.—Main flowering stem grows from base.

Foliage description:

*Leaf shape*.—Basal leaves narrow ovate, cauline leaves narrow ovate.

*Leaf division*.—Simple.

*Leaf base*.—Basal leaves and cauline leaves attenuate.

*Leaf apex*.—Basal leaves and cauline leaves narrow acute.

*Leaf venation*.—Pinnate, basal and cauline leaves; 144A in color on upper surface and 144C in color on lower surface.

*Leaf margins*.—Basal leaves and cauline leaves entire to coarsely and un-deeply dentate-crenate, non-undulate.

*Leaf attachment*.—Petiolate.

*Leaf arrangement*.—Alternate.

*Leaf size*.—Basal leaves average of 11.6 cm in length and 9.2 cm in width, cauline leaves average of 13.0 cm in length and 3.9 cm in width.

*Leaf color*.—In basal and cauline leaves: young upper surface; darker than 143A, young lower surface; 143B, mature upper surface; a color in between NN137A and 147A but slightly darker, mature lower surface; a color in between 147A and 147B.

*Leaf surface*.—Basal and cauline leaves; upper and lower surface, matte and rough to touch, very slightly rugose, with short strigose hairs; an average of 0.3 mm in length and colored white; impossible to measure with color chart due to small size and sparseness.

*Petioles*.—V-shaped, strong, basal leaves an average of 9.2 cm in length and 2 mm in diameter, cauline leaves an average of 4.0 cm in length and 2 mm in diameter, color upper surface 144B, changing towards the proximal end to 183C, margin 137A, color lower surface 144B and changing towards the proximal end to 185D, margin 137A, both surfaces smooth and glabrous.

Flower description:

*Type*.—Terminal capitulum consisting of ray florets and disc florets.

*Capitulum number*.—An average of 3 per stem, 16 per plant.

*Lastingness of inflorescence*.—A few weeks, ray florets self-cleaning.

*Capitulum size*.—Matures to about 4.1 cm in height and 10.2 cm in diameter, disc diameter is an average of 3.9 cm.

*Inflorescence aspect*.—Held straight on top of peduncles.

*Fragrance*.—Moderately faint, sweet and pleasant.

*Involucral bracts or phyllary*.—Rotate, 80 arranged spirally in four rows, average of 1.3 cm in length and 2.5 mm in width, cuneate base, acute apex, entire margin, lanceolate, strongly reflexed in shape, color upper surface NN137B and changing towards the margins and apex to 137A, color lower surface 137B, upper surface texture; smooth, lower surface texture; matte with very short strigose hairs; an average of 0.3 mm in length and too fine for color reading.

*Inflorescence buds*.—Flattened globular in shape, immature ray florets tilted upward, at an average angle of 45° to horizontal, an average of 2.7 cm in length and 4.9 cm in diameter, color 146A with immature ray florets 5D, matte surface texture.

*Peduncle*.—Strong, terminal and secondary are an average of 15 cm in length and 5 mm in diameter, terminal aspect straight on top of stem, average angle of secondary peduncles 15° (0°=straight upright), 144B in color and moderately marbled with 143C, surface is slightly to moderately to densely covered with very short strigose hairs; an average of 0.3 mm in length and 143C in color.

*Ray florets*.—Rotate around disc in 1 row, average of 26 (varying between 22 and 32) per inflorescence, oblanceolate to narrow oblong in shape, average of 4.6 cm in length and 1.1 cm in width, praemorse apex, narrow cuneate base, entire margin, held at an average angle of 10° to horizontal (=0), color; upper surface when opening 12A to 12B, and changing towards base 50B, lower surface when opening 12D and changing towards the base to 39B, upper surface when fully open 7D changing towards the tip to 1C and slightly fading at the base to 39C, lower surface when fully open 4D changing towards the tip 1B and changing towards the base to 37B, surface texture; upper and lower surface glabrous, matte and carinate.

*Disk flowers* (*bisexual*).—Numerous, average of 500, arranged spirally on disc, tubular, upright to outward aspect, apex is acute on upper 15% that is free, fused (tubular) base, entire margin, average of 9 mm in length and 2.5 mm in width, upper and lower surface textures are glabrous and glossy, color when opening and fully open upper and lower surface; apex 143A with very tip 183A, mid-section N170D, base 187D.

*Disk spines*.—Average of 500, acicular in shape, acute apex, attenuate base, glabrous and glossy surface, color is 187A changing to 45A and 23A at apex, 144B to 144C in mid region and 157D at base.

*Receptacle*.—Deltoid in shape, an average of 1.2 cm in height and diameter, and 155C in color.

Reproductive organs (present on disk florets only):

*Gynoecium*.—Pistil; average 1; 6 mm in length, style; 5 mm in length and 154D in color, stigma; unequal decurrent, in between 187A and 203C in color, ovary; 157D in color.

*Androecium*.—Stamens; 5, filaments; 3.5 mm in length and 145D in color, anthers; linear in shape, average 3.5 mm in length, N200A in color, pollen is moderate in quantity and 23A in color.

*Fruit/seed*.—No seed production has been observed to date.

It is claimed:

1. A new and distinct cultivar of *Echinacea* plant named 'Yellow Rainbow' as herein illustrated and described.

* * * * *